United States Patent
Chiu et al.

(10) Patent No.: US 7,780,930 B2
(45) Date of Patent: Aug. 24, 2010

(54) FLUOROPOLYMER LINED METALLIC VESSEL DESIGN

(75) Inventors: Yuon Chiu, Denville, NJ (US); Merwyn E. Howells, Prairieville, LA (US); Stephen A. Cottrell, Baton Rouge, LA (US)

(73) Assignee: Honeywell International, Inc., Morristown, NJ (US)

( * ) Notice: Subject to any disclaimer, the term of this patent is extended or adjusted under 35 U.S.C. 154(b) by 858 days.

(21) Appl. No.: 11/283,351

(22) Filed: Nov. 18, 2005

(65) Prior Publication Data
US 2006/0079722 A1    Apr. 13, 2006

Related U.S. Application Data

(62) Division of application No. 10/408,153, filed on Apr. 4, 2003, now Pat. No. 7,102,040.

(51) Int. Cl.
*B01J 19/00* (2006.01)
*B65D 25/16* (2006.01)
*B65D 90/04* (2006.01)

(52) U.S. Cl. ............... 422/241; 422/240; 422/129; 422/189; 422/202; 220/495.01; 220/495.04; 220/586; 220/587

(58) Field of Classification Search ............ None
See application file for complete search history.

(56) References Cited

U.S. PATENT DOCUMENTS

| | | | | |
|---|---|---|---|---|
| 2,913,318 A | * | 11/1959 | De Wet Erasmus et al. | 422/193 |
| 2,970,042 A | * | 1/1961 | Lagerwey | 422/241 |
| 3,135,420 A | | 6/1964 | Farell et al. | 220/63 |
| 3,140,006 A | * | 7/1964 | Nelson | 220/587 |
| 3,476,009 A | * | 11/1969 | Markey | 411/11 |
| 3,490,997 A | * | 1/1970 | Burney et al. | 203/7 |
| 5,246,549 A | * | 9/1993 | Heil | 203/2 |
| 5,574,192 A | | 11/1996 | VanDerPuy et al. | 570/167 |
| 5,728,904 A | | 3/1998 | VanDerPuy et al. | 570/176 |
| 5,763,706 A | | 6/1998 | Tung et al. | 570/167 |
| 5,902,912 A | | 5/1999 | Tung et al. | 570/164 |
| 6,939,521 B1 | | 9/2005 | Chiu et al. | 422/203 |

OTHER PUBLICATIONS

"Fluoropolymer-Lined Tanks and Vessels", Data Sheet, Jan. 6, 2003.
"Edlon-PSI™ Custom Linings PTFE/PFA/FEP", Data Sheet, Jan. 2000.

* cited by examiner

*Primary Examiner*—Jennifer A Leung
(74) *Attorney, Agent, or Firm*—Bruce O. Bradford

(57) ABSTRACT

The invention provides an apparatus useful in fluorinating organic compounds, or more particularly to a reactor system suitable for the fluorination of organic compounds on a commercial scale. The apparatus is also useful in chemical reactions including heating or cooling.

14 Claims, 3 Drawing Sheets

FLUOROPOLYMER LINED METALLIC VESSEL DESIGN

CROSS REFERENCE TO RELATED APPLICATION

This application is a division of U.S. patent application Ser. No. 10/408,153, filed Apr. 4, 2003, now U.S. Pat. No. 7,102,040, which is incorporated herein by reference.

BACKGROUND OF THE INVENTION

The present invention relates to an apparatus useful for fluorinating organic compounds, or more particularly to a reactor suitable for the fluorination of organic compounds on a commercial scale. The reactor may also be used for other chemical processing that require heating or cooling. The reactor finds particular use in the manufacture of hydroflurocarbons (HFCs). The reactor of the invention includes a large volume reactor vessel lined with a loose fluoropolymer liner that is highly resistive to corrosion.

It is known in the art that hydrofluorocarbons (HFCs) are popular substitutes for chlorofluorocarbons (CFCs) and hydrochlorofluorocarbons (HCFCs) for use as refrigerants, heat transfer agents, blowing agents and propellants because HFCs do not deplete the ozone layer of the atmosphere. HFCs are typically prepared by fluorinating a chlorinated organic compound with a fluorination agent such as hydrogen fluoride in the presence of a fluorination catalyst. This reaction may be conducted in either the liquid or gas phase. Generally, the liquid phase fluorination process is preferred because the reaction is controlled at relatively lower temperatures which results in less by-product formation due to decomposition.

Liquid phase fluorination, however, uses and generates corrosive compounds, such as hydrogen fluoride, hydrogen chloride, and Lewis acid catalysts, which form superacids. These superacids tend to corrode the reactor vessel in which the reaction is conducted, even reactors comprised of corrosion-resistant materials such as Inconel 600, NAR25-50MII, Hastelloy C, Hastelloy G-30, duplex stainless steel, and Hastelloy C-22. Corrosion of the reactor compromises the structural integrity of the reactor and reduces its useful life. Therefore, a need exists to minimize reactor corrosion.

One method of reducing such corrosion is taught in Japanese Kokai Patent Application Publication No. 233102(1995). In this publication, a method is disclosed for the liquid phase fluorination of a chlorinated organic compound in a reactor made or lined with a fluorine containing resin. The method involves gaseous feeds of hydrogen fluoride and chlorinated organic compound. Because the process is restricted to gaseous feed streams, it is limited in the type of HFCs it can produce. Chlorinated organic compounds having two or more carbon atoms tend to decompose before reaching their gaseous state. Thus, as a practical matter, the process disclosed in this publication can only be used to produce fluorinated methanes.

The aforementioned Japanese publication also states that when heat transfer through the reactor is necessary, which is usually the case in liquid phase fluorination, the fluorine containing resin liner should be applied using a molding method. The only molding method identified therein is rotary-baked molding.

Generally, reactors having a molded liner, such as a rotary-baked or sprayed-on liner, are not suitable for large-scale commercial production. Reactors having such liners must be baked in large kilns or ovens, which are expensive and frequently unavailable. Indeed, fitting a large reactor, for example, greater than about a 1,000 gallons, with a baked liner is impractical.

A molded liner not only imposes practical limitations on the reactor, but also introduces structural limitations. It has been found that molded liners tend to be permeable and, under high pressures and over time, reactants tend to penetrate the liner and develop pressure between the liner and the reactor wall. Therefore, while a rotary-baked, fluorine-resin liner may minimize reactor corrosion, its structural limitations nevertheless limit the reactor's useful lifetime.

To overcome these problems which are inherent with rotary-baked or spray molded liners, it is now popular in the art to use a loose liner to line the inside of reactors. As the term implies, a loose lining is one which is fabricated from a sheet of protective material in a desired configuration and which is then installed into the intended equipment. Capped flanges on the ends of the vessel are typically used to pressure fix the ends of the lining to the ends of the vessel.

Regarding fluorination reactions in particular, reactors that are lined with a loose lining fabricated from fluoropolymer materials have been found to be useful for combating the corrosive conditions present in certain small-scale liquid phase fluorination reactions. For example, U.S. Pat. No. 5,902,912 teaches using a 50 gallon (appx. 6.7 ft$^3$) loosely lined reactor vessel for producing less than one million lbs/yr of fluorocarbons in pilot scale operations. However, it has been determined that conventional non-corroding, fluoropolymer-lined reactors suffer from a variety of problems when utilized in large-volume processes, e.g. at least about 1000 gallons (appx. 134 ft$^3$). Such problems include body flange seal leaking, liner flexing stress and shrinking, as well as leakage of hydrogen fluoride through the liner. Therefore, a need exists for non-corrosive reactors that can be used for the commercial scale production of fluorinated compounds. More particularly, there is a need for a high integrity, fluoropolymer lined metallic vessel having a heat input/output capability suitable to manufacture HFCs, such as HFC-143a, HFC-32, HFC-245fa, HFC-227ea, HFC-236fa, HFC-365mfc, etc., and to conduct other highly corrosive applications on a commercial scale.

The present invention provides a non-corroding and highly reliable apparatus useful for liquid phase hydrofluorination of organic compounds. Furthermore, the invention provides a reactor apparatus that avoids the problem of liner flexing and shrinking during disassembly of the reactor, and thus extending the operational life of the liner.

DESCRIPTION OF THE INVENTION

Figure 1:
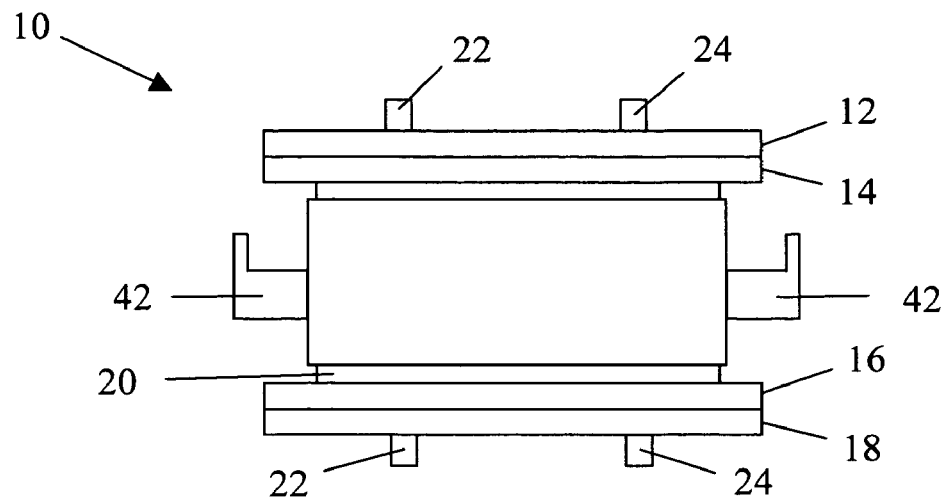
FIG. 1 is a side-view of a single stage reactor apparatus having one shell member.

The invention provides a reactor apparatus comprising:
a) a vessel comprising (i) or (ii):
i.) a single shell member
said shell member having a circumferential wall with an inner surface which defines an interior cavity within the inner surface; said shell member having a top shell member opening at a top of the circumferential wall and a bottom shell member opening at a bottom of the circumferential wall, a first flange integrally formed with the shell member around the circumferential wall at the top shell member opening, which first flange extends outwardly perpendicularly from the circumferential wall; a second flange integrally formed with the shell member around the circumferential wall at the bottom shell member opening, which second flange extends outwardly perpendicularly from the circumferential wall;
ii) a plurality of sequentially attached shell members,
each shell member having a circumferential wall with an inner surface which defines an interior cavity within the inner surface; each shell member having a top shell member opening at a top of the circumferential wall and a bottom shell member opening at a bottom of the circumferential wall, a first flange integrally formed with the shell member around the circumferential wall at the top shell member opening, which first flange extends outwardly perpendicularly from the circumferential wall; a second flange integrally formed with the shell member around the circumferential wall at the bottom shell member opening, which second flange extends outwardly perpendicularly from the circumferential wall;
the shell members being sequentially attached by mating adjacent shell member flanges with an array of bolt and washer combinations extending around and through the adjacent shell member flanges; an intermediate gasket being positioned between mating adjacent shell member flanges, said intermediate gasket being positioned between the circumferential wall to the circular array of bolt and washer combinations;
said vessel having a top opening at a top end thereof which is an uppermost top shell member opening, and a bottom opening at a bottom end thereof which is a lowermost bottom shell member opening;
b) a loose fluoropolymer liner lining the entire inner surface of each circumferential wall;
c) a top cover on the entire top opening of the vessel and on an uppermost of the shell member flanges, which top cover has an inner surface positioned on a first gasket, the first gasket being positioned on the uppermost shell member flange and said first gasket being separated from the uppermost shell member flange by a first end of the liner; the top cover being attached to the uppermost shell member flange by an circular array of bolt and washer combinations extending around and through both the top cover and the uppermost shell member flange, said circular array of bolt and washer combinations being positioned between the circumferential wall and a terminal edge of the uppermost shell member flange; said first gasket being positioned between the circumferential wall to the circular array of bolt and washer combinations;
d) a bottom cover on the entire bottom opening of the vessel and on a lowermost of the shell member flanges, which bottom cover has an inner surface positioned on a second gasket, the second gasket being positioned on the lowermost shell member flange and said second gasket being separated from the lowermost shell member flange by a second end of the liner; the bottom cover being attached to the lowermost shell member flange by a circular array of bolt and washer combinations extending around and through both the bottom cover and the lowermost shell member flange, said circular array of bolt and washer combinations being positioned between the circumferential wall and a terminal edge of the lowermost shell member flange; said second gasket being positioned between the circumferential wall to the circular array of bolt and washer combinations;
e) a first end of the liner being attached to the uppermost shell member flange by a circular array of screw fasteners extending around and through the uppermost shell member flange, which fasteners are positioned between the circular array of bolt and washer combinations and the terminal edge of the uppermost shell member flange; and a second end of the liner being attached to the lowermost shell member flange by a circular array of screw fasteners extending around and through the lowermost shell member flange positioned between the circular array of bolt and washer combinations and a terminal edge of the lowermost shell member flange;
f) at least one inlet for supplying at least one fluid into said interior cavity; and
g) at least one outlet for discharging at least one fluid from said interior cavity.

The invention also provides a hydrofluorination process comprising:
I) providing a reactor apparatus as described above;
II) supplying a chlorinated organic material into said vessel through said at least one inlet;
III) supplying hydrogen fluoride into said vessel through said at least one inlet; and
IV) reacting the chlorinated organic material with said hydrogen fluoride to form a hydrofluorocarbon.

The invention further provides a process for forming hydrofluorocarbons, such as HFC-143a, HFC-32, HFC-245fa, HFC-227ea, HFC-236fa, HFC-365mfc, but not limited to these HFCs, by using the apparatus of the invention.

The invention still further provides a reaction process comprising:
I) providing a reactor apparatus comprising:
a) a vessel comprising (i) or (ii):
i.) a single shell member
said shell member having a circumferential wall with an inner surface which defines an interior cavity within the inner surface; said shell member having a top shell member opening at a top of the circumferential wall and a bottom shell member opening at a bottom of the circumferential wall, a first flange integrally formed with the shell member around the circumferential wall at the top shell member opening, which first flange extends outwardly perpendicularly from the circumferential wall; a second flange integrally formed with the shell member around the circumferential wall at the bottom shell member opening, which second flange extends outwardly perpendicularly from the circumferential wall;
ii) a plurality of sequentially attached shell members,
each shell member having a circumferential wall with an inner surface which defines an interior cavity within the inner surface; each shell member having a top shell member opening at a top of the circumferential wall and a bottom shell member opening at a bottom of the circumferential wall, a first flange integrally formed with the shell member around the circumferential wall at the top shell member opening, which first flange extends outwardly perpendicularly from the circumferential wall; a second flange integrally formed with the shell member around the circumferential wall at the bottom shell member opening, which second flange extends outwardly perpendicularly from the circumferential wall;

the shell members being sequentially attached by mating adjacent shell member flanges with an array of bolt and washer combinations extending around and through the adjacent shell member flanges; an intermediate gasket being positioned between mating adjacent shell member flanges, said intermediate gasket being positioned between the circumferential wall to the circular array of bolt and washer combinations;

said vessel having a top opening at a top end thereof which is an uppermost top shell member opening, and a bottom opening at a bottom end thereof which is a lowermost bottom shell member opening;

b) a loose fluoropolymer liner lining the entire inner surface of each circumferential wall;

c) a top cover on the entire top opening of the vessel and on an uppermost of the shell member flanges, which top cover has an inner surface positioned on a first gasket, the first gasket being positioned on the uppermost shell member flange and said first gasket being separated from the uppermost shell member flange by a first end of the liner; the top cover being attached to the uppermost shell member flange by an circular array of bolt and washer combinations extending around and through both the top cover and the uppermost shell member flange, said circular array of bolt and washer combinations being positioned between the circumferential wall and a terminal edge of the uppermost shell member flange; said first gasket being positioned between the circumferential wall to the circular array of bolt and washer combinations;

d) a bottom cover on the entire bottom opening of the vessel and on a lowermost of the shell member flanges, which bottom cover has an inner surface positioned on a second gasket, the second gasket being positioned on the lowermost shell member flange and said second gasket being separated from the lowermost shell member flange by a second end of the liner; the bottom cover being attached to the lowermost shell member flange by a circular array of bolt and washer combinations extending around and through both the bottom cover and the lowermost shell member flange, said circular array of bolt and washer combinations being positioned between the circumferential wall and a terminal edge of the lowermost shell member flange; said second gasket being positioned between the circumferential wall to the circular array of bolt and washer combinations;

e) a first end of the liner being attached to the uppermost shell member flange by a circular array of screw fasteners extending around and through the uppermost shell member flange, which fasteners are positioned between the circular array of bolt and washer combinations and the terminal edge of the uppermost shell member flange; and a second end of the liner being attached to the lowermost shell member flange by a circular array of screw fasteners extending around and through the lowermost shell member flange positioned between the circular array of bolt and washer combinations and a terminal edge of the lowermost shell member flange;

f) at least one inlet for supplying at least one fluid into said interior cavity; and g) at least one outlet for discharging at least one fluid from said interior cavity.

II) supplying a first reagent into said vessel through at least one inlet;

III) supplying a second into said vessel through said at least one inlet; and

IV) reacting the first reagent with the second reagent to form a reaction product.

The reactor is suitable for conducting high integrity chemical processing under high pressures and high temperature, and for heat transferring under high pressures. Such processes include either liquid or gaseous phase fluorination, but the reactor is especially suited for sustaining the extremely corrosive conditions of liquid fluorination reactions.

As shown in FIG. 1, the reactor 10 comprises one circumferential, metallic shell member 20 that defines an interior cavity 38 (FIG. 4) into which reactants are supplied. Metallic shell can be made of any types of metal as long as it can provide mechanical strength. Corrosion-resistant metals or metal alloys, such as stainless steel, nickel containing alloys such as Inconel alloys, Monel alloys, Hastelloys, and combinations thereof. are preferred. It is also preferred that the shell members of the invention are equipped with a carbon steel wall jacket. The shell member preferably has an internal diameter of from about 4.0 feet to about 6 feet. However, the diameter may be wider or narrower.

The shell member 20 has a top opening at a top end and a bottom opening at a bottom end, with each end being sealed by a top cover 12 and a bottom cover 18, respectively. Each cover is either flat or curved in shape and functions to seal their respective openings. In the preferred embodiment of the invention, each of the top cover 12 and bottom cover 18 are flat to minimize liner welds. Each cover preferably comprises a solid metallic plate of approximately ¼ inch (6.35 mm) in thickness fabricated from the same metal as the shell member (e.g. a nickel alloy). The metallic plate is then plug welded to a carbon steel backup plate.

Extending through the top cover 12 and into the interior cavity 38 is an inlet 22 which supplies fluids or gases or both into the interior cavity. Also extending through the top cover 12 and into the cavity 38 is an outlet 24 which allows for discharging fluids or gases or both from the cavity 38. As seen in the figure, the reactor apparatus may similarly include an inlet 22 and an outlet 24 extending through the bottom cover 14 and into the cavity 38. While reference is made herein to inlets and outlets in general terms, it should be understood that the inlets and outlets are simply access points through which a gas or fluid may be either supplied to or discharged from the inside of the reactor vessel. Each inlet or outlet may vary in diameter size and each is to be equipped with a nozzle. The reactor apparatus may also include additional inlets and/or outlets as desired to maintain the integrity of the reactor apparatus and as required by particular reaction processes. It is preferable that the reactor apparatus be equipped with one or more 2 to 6 inch (5.08 to 15.24 cm) wide reactor feed inlets, a 2 to 6 inch (5.08 to 15.24 cm) purge inlet, and an 12 to 30 inch (30.48 to 76.2 cm) reaction vapor outlet. Each shell members may also be equipped with at least one 1 to 3 inch (2.54 to 7.62 cm) steam inlet and at least one 1 to 3 inch (2.54 to 7.62 cm) condensate outlet. Either the top cover 12 or bottom cover 18 or both may further be equipped with meters that measure the pressure and/or temperature conditions within the reactor apparatus. For example, a reactor apparatus may be equipped with an inlet/outlet through which is attached a pressure gauge, and another through which is attached a temperature gauge. The reactor apparatus may also be equipped with sampling mounts as desired.

Integrally formed with the shell 20 at its top end and adjacent to the top cover 12 is a first flange 14. Similarly, a second flange 16 is formed with the shell 20 at its bottom end, the second flange 16 being adjacent to the bottom cover 18.

Figure 3:
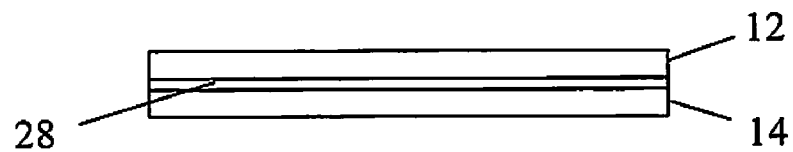
FIG. 3 is a side view of two adjacent flanges having an intermediate gasket.

Positioned between the top cover 12 and the first flange 14, as well as between the second flange 16 and the bottom cover 18, is a gasket 28 as can be seen in FIG. 3. Each of the flanges is preferably comprised of the same metal used to form the shell members and covers. Suitable gasket materials include fluoropolymer materials, such as polytrifluoroethylene (e.g. TaskLine® gaskets) or polychlorotrifluoroethylene, and is preferably a high compressibility fluoroplastic tape, e.g. Gortex® tape. Utilizing such high compressibility fluoroplastic tape compensates for any unevenness of the liner between the flange joints. In the preferred embodiment of the invention, each flange is at least twice the gasketing width. These extra wide flanges add extra support to the liner and helps to prevent shrinkage of the liner. The gasket should extend from a point between the edge of cavity 38 up to the edge of the bolts holes which attach the flanges 14 and 16 to their respective covers 12 and 18.

Figure 2:
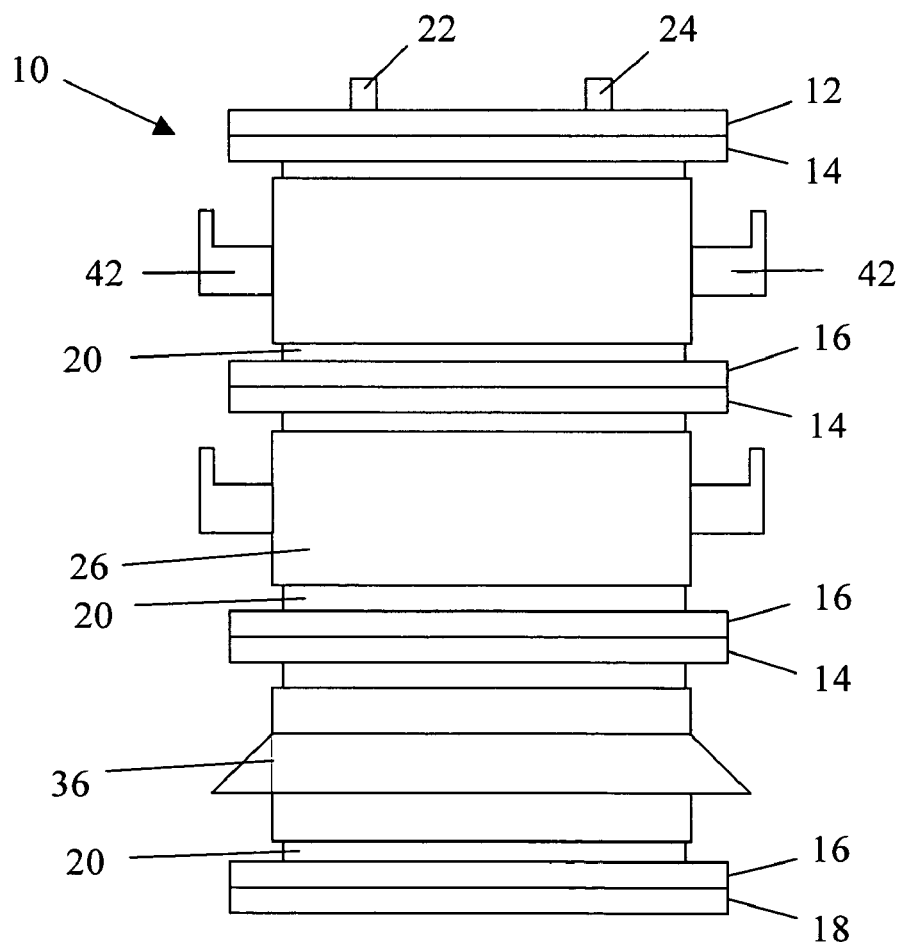
FIG. 2 is a side-view of a multi-stage reactor apparatus having a plurality of shell members.

In the preferred embodiment of the invention, the shell member 20 along with first flange 14 and second flange 16 is formed such that size of the reactor apparatus may be expanded by adding additional shell members 20. This embodiment is shown in FIG. 2. As seen in the figure, additional shell members 20 may be added such that the second (bottom) flange 16 mates with the first (top) flange 14 of an adjacent shell member. As shown in FIG. 3, two adjacent flanges are also separated by a gasket 28. In the preferred embodiment of the invention, each flange is at least about twice the width of the gaskets. Each of these shell members are substantially identical to each other, including the supports and fittings, and are the shell members are interchangeable.

While FIG. 2 illustrates an example of a reactor having three shell members 20 joined together to form a single reactor vessel, it should be understood that the reactor apparatus 10 may include more or fewer than three shell members 20. Preferably the overall size of the reactor apparatus 10 is such that the interior cavity 38 contains a volume of about 10 ft$^3$ or more. In the preferred embodiment of the invention, each of the shell members with its integrally formed flanges preferably has a length of from about 7 feet to about 8 feet. However, it should be understood that each shell member may be longer or shorter in length.

Figure 4:
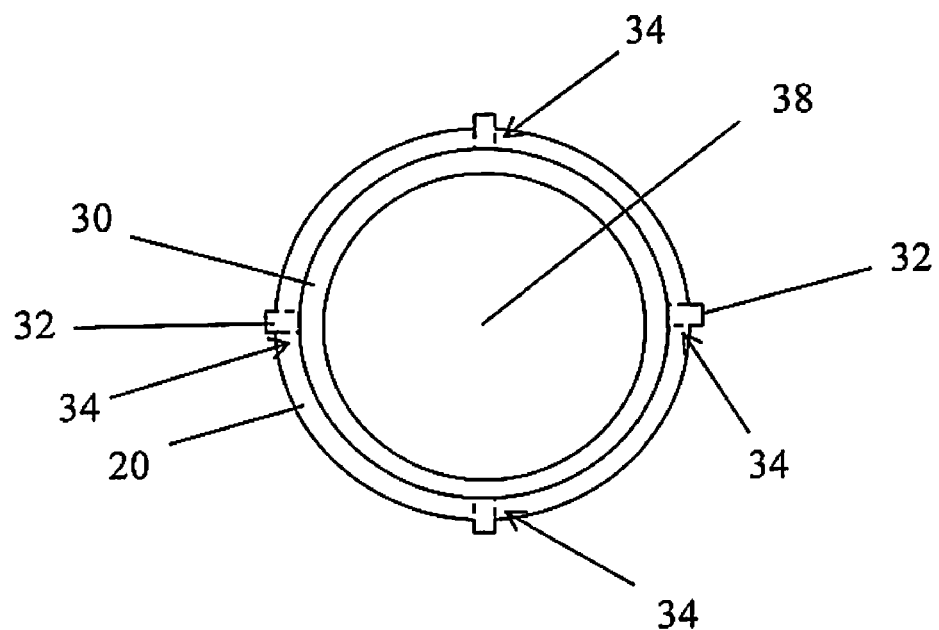
FIG. 4 is a top view of an open reactor apparatus having a weep-hole.

Lining all exposed interior surfaces of the reactor, including the inner surfaces of each of the top cover 12 and the bottom cover 18, is a loose fluoropolymer liner 30, shown in FIG. 4. As used herein, a "loose fluoropolymer liner" broadly refers to a liner which is fitted from a film or sheet of a fluoropolymer material and which covers the inner metallic surfaces of the reactor. Specifically, the liner 30 insulates all internal metal surfaces from corrosive reactants or reaction products present inside the reactor, but is not permanently molded to the reactor. A loose liner differs from a molded liner in that a loose liner is not sprayed-on or rotary-baked from liquid form, but is a pre-fabricated sheet material which is supported in the reactor. As is known in the art, molded liners are coated onto the entire inside surface of a reactor vessel and are generally useful in small scale manufacturing applications. However, molded liners are very expensive to fabricate and are impractical for fitting large reactors. One main problem with molded liners is that they are known to break down structurally when placed under high pressures and when used over a long period of time. On the other hand, a loose liner is capable of withstanding very high pressures and very high temperatures, and is easily replaceable. Additionally, a loose liner is less porous than molded liners, has better overall strength and is not limited in thickness.

The loose liner 30 is positioned into the reactor vessel using conventional application techniques, and is flared between two adjacent flanges 14 and 16 (or between top cover 12 and flange 14 and between flange 16 and bottom cover 18) such that the flanges fix the liner to the vessel. As mentioned above, the flanges are at least about twice as wide as the gasket between the flanges. Flanges that are at least about twice as wide as the gasket width allow for self-regulating sealing pressure and reduces liner stress at the flange joints. This also avoids over-compressing the liner 30 between the flanges, yet maximizes the reliability of the gasket sealability. It is also within the preferred embodiment of the invention that the liner 30 is secured in place with secondary fasteners to hold the liner 30 in place during disassembly of the reactor apparatus 10.

Figure 6:
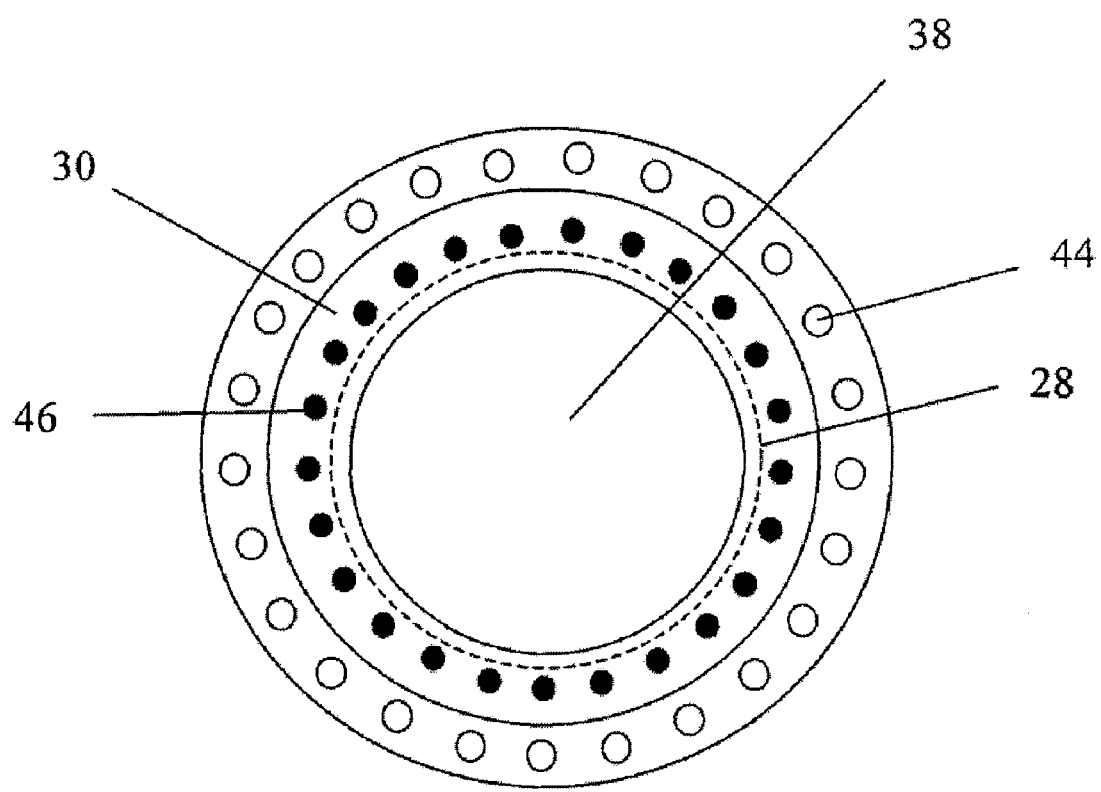
FIG. 6 is a top cross-sectional view of the reactor apparatus showing the sequential bolting of the flanges and the secondary fasteners for the lining.

As shown in FIG. 6, further supporting the liner in the vessel are a plurality of secondary fasteners 46, preferably fastening screws that penetrate through the liner and are fixed to the flanges. The liner is initially fixed to the vessel at the flanges whereby a portion of the liner is flared onto a surface of one flange, wherein a second flange (or a cover) is then pressed onto the first flange, thus holding the liner between the two flanges. The dotted line shown in FIG. 6 represents the boundary of the gasket 28, which preferably only extends from the edge of interior cavity 38 to the edge of bolt holes 44. As also shown in the figure, the secondary fasteners 46 are then inserted through the liner and connected to at least one of the adjacent flanges to further support the liner against the flange.

These fasteners 46 function primarily to hold the liner in place during disassembly. This is an especially advantageous feature of the invention because it avoids complications associated with liner shrinking. More specifically, it has been found that upon disassembly of a reactor apparatus having a loose fluoropolymer liner that has experienced some extended use, the liner has exhibited some shrinkage in size. Accordingly, once the liner is released from its fixed position between adjacent flanges, the liner no longer fits and cannot be replaced upon reassembly of the reactor apparatus. Therefore, a new liner must be fitted to the vessel, which is very costly. It has been unexpectedly found that by further securing the liner 30 with such an array of secondary fasteners 46 that the liner may be held in place during disassembly of the reactor apparatus, preventing any recoil and shrinkage of the liner. The secondary fasteners 46 are preferably positioned between the bolt holes 44 and the outermost edge of the flange. In order to confirm the tightness of the liner to the flange joint and provide quality assurance to the final reactor installation, a hydrotest of the liner may be conducted.

In the preferred embodiment of the invention, the fluoropolymer liner preferably comprises a polymer selected from the group consisting of, but not limited to, fluorinated ethylene propylene, poly(vinylidene fluoride), polytetrafluoroethylene, perfluoroalkoxy polymer, ethylene tetrafluoroethylene, ethylene hexafluoropropylene, tetrafluoroethylene-hexafluoropropylene, polychlorotrifluoroethylene, ethylene chlorotrifluoroethylene and combinations thereof. Of these, polytrifluoroethylene and perfluoroalkoxy copolymer are the most preferred fluoropolymers. In the preferred embodiment of the invention, the liner sheet has a thickness of about 0.5 mm to about 15 mm, more preferably from about 3 mm to about 13 mm, and most preferably from about 5 to about 10 mm. However, it should be understood that such thicknesses may vary as determined by individual uses and applications of the reactor apparatus.

As illustrated in FIG. 6, the flanges are bolted together through bolt holes 44 using an circular array of bolt and washer combinations extending around and through the flanges. Sequential bolt torqueing around the flanges provides an evenly distributed bolting force on the flange sealing gaskets. The bolt seals are preferably continuously monitored by an on-stream ultrasonic bolt load monitoring system. Such monitoring provides instant and constant monitoring of the integrity of the flange seals, allowing for preventive measurements against the formation of leaks. In addition, in order to reduce costs, torsion torque control may be used for practical tightening using inexpensive air-driven impact wrenches.

Figure 5:
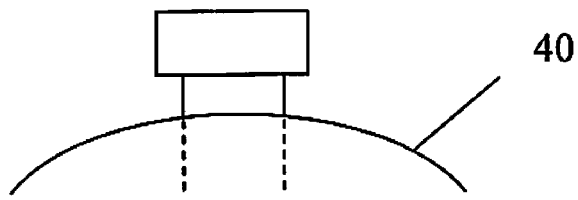
FIG. 5 is a side view schematic representation of a bolt through a spring-loaded washer.

Positioned between each bolt and each flange are spring-loaded washers 40. This can be seen in FIG. 5. A spring loaded washer is a compact spring in the shape of a washer that has been pressed into a dished shape and then hardened and tempered. One particularly preferred spring loaded washer for use in assembling the reactor apparatus is a Belleville washer. A Belleville washer is a disk spring that applies pressure to the connection once you clamp down on it with the proper amount of force. The advantage of this washer is that it applies clamping pressure along a continuous arc pattern, instead of concentrating it at one point. Additionally, such Belleville washers provide predictable bolting forces and maintains a positive sealing after the reactor has experienced numerous repeated cycles of pressure and temperature changes.

In the preferred embodiment of the invention, the initial cold bolting force on the spring washers is preferably from about 2,000 to about 40,000 lbs. force/bolt, more preferably from about 10,000 to about 33,000 lbs. force/bolt and most preferably from about 20,000 to about 23,000 lbs. force/bolt.

In the preferred embodiment of the invention each shell member 20 includes at least one weep hole 34 extending through the shell and to the surface of the liner, and preferably a plurality of weep holes as seen in FIG. 4. These weep holes 34 are holes in the shell that allow reactants that permeate the fluoropolymer lining be vented out of the reactor. This prevents reactants from building up pressure between the liner and the shell wall and forming blisters in the liner. The weep holes are preferably from about 4.5 mm to about 10 mm in diameter, more preferably from about 5.5 mm to about 8.5 mm, most preferably from about 6.5 mm to about 8 mm. In the most preferred embodiment of the invention, each shell member 20 includes at least eight weep holes. As illustrated in FIG. 4, it is preferred that each shell member has four weep holes at each of its top and bottom ends, with each weep hole being separated from the next by 90° along the circumference of the shell member. Each of the inlets and outlets are preferably also provided with a weep hole. Each weep hole 34 is preferably equipped with a ⅜ inch to 1½ inch (0.95 to 3.8 cm) NPT coupling. Each coupling is preferably comprised of the same metal used to form the shell member.

In the preferred embodiment of the invention, the weep holes are equipped with fluoroplastic inserts 32 that extend to the inner surface of the shell and reinforce the unsupported liner spots at the weep holes 34. The fluoroplastic inserts 32 preferably comprise a fluoropolymer material selected from the group listed above. It is also preferred that the reactor apparatus further include an active vacuum system that is connected to the weep hole system to prevent a vacuum collapse of the liner. This vacuum system prevents liner damage from vacuum collapsing in the event of improper operation of the reactor.

The reactor is also capable of being heated or cooled well enough to keep the reaction temperature at a set, desired temperature, as well as at a desired pressure. In order to heat or cool the vessel, the reactor apparatus is equipped with jackets 26. Jackets 26, as shown in FIGS. 1 and 2, preferably surround each shell member, and allow for controlled heating or cooling of the vessel. Jackets 26 are preferably spaced from the flanges to minimize excessive heating of the liner. In the preferred embodiment of the invention, the steam jacket is maintained at an operating temperature of from about 40° C. to about and 375° C., more preferably from about 65° C. to about 190° C. and most preferably from about 100° C. to about 155° C. The reactor is also preferably maintained at an operating pressure of from about 15 psig to about 350 psig, preferably from about 30 psig to about 250 psig and more preferably from about 75 psig to about 200 psig. As also shown in FIG. 2, jackets 26 are preferably supported by a support lug 36. While only a single support lug 36 is shown in FIG. 2, it is preferred that each steam jacket 26 is supported by a separate support lug 36.

The reactor apparatus of the invention may further include additional features that are conventionally used for supporting a reactor apparatus or for further securing joints. For example, as shown in FIGS. 1 and 2, the reactor apparatus of the invention may include unit lifting and/or unit tailing trunions 42 at selected locations on the outer body of the reactor apparatus. The reactor apparatus may further include other conventional features that are not shown in the drawings. For example, each of the covers and flanges preferably include lift lugs (at least two with pads on each section of the apparatus), ground lugs (at least two) and detector mounting clips that aid in the disassembly and/or moving of the apparatus. Further, all carbon steel attachments to a nickel alloy must include an attachment pad having a minimum thickness of ¼ inch (6.35 mm).

It should be understood that the reactor apparatus may also include additional features not specifically mentioned herein as may be conventionally known by one skilled in the art, particularly features useful for disassembling and moving the reactor apparatus.

The following non-limiting example serves to illustrate the invention.

EXAMPLE 1

A reactor apparatus is constructed as described above and having a 3,000 gallon interior volume (11,353 Liters). The reactor is pre-charged with antimony pentachloride catalyst. A chlorinated organic and hydrogen fluoride are then introduced into the reactor. The operating reactions of the reactor are set to 160 psig and 220° F. (104.4° C.), and steam is introduced on the steam jacket to heat the reactor. The process yields at least 1,000 lb/hr (7.6 kg/min) of a hydrofluorocarbon, and accumulates at least 2000 hours of operating time without leaks or liner damage.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:
1. A reactor apparatus comprising:
(a) a vessel comprising (x) or (y):
(x) a single shell member
the shell member having a circumferential wall with an inner surface which defines an interior cavity within the inner surface;

the shell member having a top shell member opening at a top of the circumferential wall and a bottom shell member opening at a bottom of the circumferential wall, a first flange integrally formed with the shell member around the circumferential wall at the top shell member opening, wherein the first flange extends outwardly perpendicularly from the circumferential wall;

a second flange integrally formed with the shell member around the circumferential wall at the bottom shell member opening, wherein the second flange extends outwardly perpendicularly from the circumferential wall;

(y) a plurality of sequentially attached shell members, each shell member having a circumferential wall with an inner surface which defines an interior cavity within the inner surface;

each shell member having a top shell member opening at a top of the circumferential wall and a bottom shell member opening at a bottom of the circumferential wall, a first flange integrally formed with the shell member around the circumferential wall at the top shell member opening, wherein the first flange extends outwardly perpendicularly from the circumferential wall;

a second flange integrally formed with the shell member around the circumferential wall at the bottom shell member opening, wherein the second flange extends outwardly perpendicularly from the circumferential wall;

the shell members being sequentially attached by mating adjacent shell member flanges with an array of bolt and washer combinations extending around and through the adjacent shell member flanges;

an intermediate gasket being positioned between mating adjacent shell member flanges, each intermediate gasket being positioned between the circumferential wall to the circular array of bolt and washer combinations;

the vessel having a top opening at a top end thereof which is an uppermost top shell member opening, and a bottom opening at a bottom end thereof which is a lowermost bottom shell member opening;

(b) a loose fluoropolymer liner lining the entire inner surface of each circumferential wall;

(c) a top cover on the entire top opening of the vessel and on an uppermost of the shell member flanges, wherein the top cover has an inner surface positioned on a first gasket, the first gasket being positioned on the uppermost shell member flange and the first gasket being separated from the uppermost shell member flange by a first end of the liner;

the top cover being attached to the uppermost shell member flange by a circular array of bolt and washer combinations extending around and through both the top cover and the uppermost shell member flange, the circular array of bolt and washer combinations being positioned between the circumferential wall and a terminal edge of the uppermost shell member flange;

the first gasket being positioned between the circumferential wall to the circular array of bolt and washer combinations;

(d) a bottom cover on the entire bottom opening of the vessel and on a lowermost of the shell member flanges, wherein the bottom cover has an inner surface positioned on a second gasket, the second gasket being positioned on the lowermost shell member flange and the second gasket being separated from the lowermost shell member flange by a second end of the liner;

the bottom cover being attached to the lowermost shell member flange by a circular array of bolt and washer combinations extending around and through both the bottom cover and the lowermost shell member flange, the circular array of bolt and washer combinations being positioned between the circumferential wall and a terminal edge of the lowermost shell member flange;

the second gasket being positioned between the circumferential wall to the circular array of bolt and washer combinations;

(e) a first end of the liner being attached to the uppermost shell member flange by a circular array of screw fasteners extending around and through the uppermost shell member flange, wherein the fasteners are positioned between the circular array of bolt and washer combinations and the terminal edge of the uppermost shell member flange; and a second end of the liner being attached to the lowermost shell member flange by a circular array of screw fasteners extending around and through the lowermost shell member flange positioned between the circular array of bolt and washer combinations and a terminal edge of the lowermost shell member flange;

(f) at least one inlet for supplying at least one fluid into the interior cavity;

(g) at least one outlet for discharging at least one fluid from the interior cavity;

(h) wherein at least one shell further comprises at least one weep hole capable of transmitting gases from between the interior cavity of the vessel and the liner to the outside of the vessel, and (i) wherein the at least one weep hole further comprises at least one fluoropolymer insert which extends through the weep hole and into the vessel.

2. A reactor apparatus comprising:

(a) a vessel comprising a single shell member;

the shell member having a circumferential wall with an inner surface which defines an interior cavity within the inner surface;

the shell member having a top shell member opening at a top of the circumferential wall and a bottom shell member opening at a bottom of the circumferential wall;

a first flange integrally formed with the shell member around the circumferential wall at the top shell member opening, wherein the first flange extends outwardly perpendicularly from the circumferential wall;

a second flange integrally formed with the shell member around the circumferential wall at the bottom shell member opening, wherein the second flange extends outwardly perpendicularly from the circumferential wall;

(b) a loose fluoropolymer liner lining the entire inner surface of the circumferential wall, wherein the liner is held in position such that recoil and shrinkage are prevented during disassembly of the reactor;

(c) a top cover on the entire top opening of the vessel and on an uppermost of the shell member flanges, wherein the top cover has an inner surface positioned on a first gasket;

the first gasket being positioned on the uppermost shell member flange and the first gasket being separated from the uppermost shell member flange by a first end of the liner;

the top cover being attached to the uppermost shell member flange by a circular array of bolt and washer combinations extending around and through both the top cover and the uppermost shell member flange;

the circular array of bolt and washer combinations being positioned between the circumferential wall and a terminal edge of the uppermost shell member flange;

the first gasket being positioned between the circumferential wall to the circular array of bolt and washer combinations;

(d) a bottom cover on the entire bottom opening of the vessel and on a lowermost of the shell member flanges, wherein the bottom cover has an inner surface positioned on a second gasket;

the second gasket being positioned on the lowermost shell member flange and the second gasket being separated from the lowermost shell member flange by a second end of the liner;

the bottom cover being attached to the lowermost shell member flange by a circular array of bolt and washer combinations extending around and through both the bottom cover and the lowermost shell member flange;

the circular array of bolt and washer combinations being positioned between the circumferential wall and a terminal edge of the lowermost shell member flange;

the second gasket being positioned between the circumferential wall to the circular array of bolt and washer combinations;

(e) a first end of the liner being attached to the uppermost shell member flange by a circular array of screw fasteners extending around and through the uppermost shell member flange, wherein the fasteners are positioned between the circular array of bolt and washer combinations and the terminal edge of the uppermost shell member flange;

a second end of the liner being attached to the lowermost shell member flange by a circular array of screw fasteners extending around and through the lowermost shell member flange positioned between the circular array of bolt and washer combinations and a terminal edge of the lowermost shell member flange;

(f) at least one inlet for supplying at least one fluid into the interior cavity;

(g) at least one outlet for discharging at least one fluid from the interior cavity;

(h) wherein the shell further comprises at least one weep hole capable of transmitting gases from between the interior cavity of the vessel and the liner to the outside of the vessel; and (i) wherein the at least one weep hole further comprises at least one fluoropolymer insert which extends through the weep hole and into the vessel.

3. A reactor apparatus comprising:

(a) a vessel comprising a plurality of sequentially attached shell members, each shell member having a circumferential wall with an inner surface which defines an interior cavity within the inner surface;

each shell member having a top shell member opening at a top of the circumferential wall and a bottom shell member opening at a bottom of the circumferential wall;

a first flange integrally formed with the shell member around the circumferential wall at the top shell member opening, wherein the first flange extends outwardly perpendicularly from the circumferential wall;

a second flange integrally formed with the shell member around the circumferential wall at the bottom shell member opening, wherein the second flange extends outwardly perpendicularly from the circumferential wall;

the shell members being sequentially attached by mating adjacent shell member flanges with an array of bolt and washer combinations extending around and through the adjacent shell member flanges;

an intermediate gasket being positioned between mating adjacent shell member flanges;

the intermediate gasket being positioned between the circumferential wall to the circular array of bolt and washer combinations;

the vessel having a top opening at a top end thereof which is an uppermost top shell member opening, and a bottom opening at a bottom end thereof which is a lowermost bottom shell member opening;

(b) a loose fluoropolymer liner lining the entire inner surface of each circumferential wall, wherein the liner is held in position such that recoil and shrinkage are prevented during disassembly of the reactor;

(c) a top cover on the entire top opening of the vessel and on an uppermost of the shell member flanges, wherein the top cover has an inner surface positioned on a first gasket, the first gasket being positioned on the uppermost shell member flange and the first gasket being separated from the uppermost shell member flange by a first end of the liner;

the top cover being attached to the uppermost shell member flange by a circular array of bolt and washer combinations extending around and through both the top cover and the uppermost shell member flange, the circular array of bolt and washer combinations being positioned between the circumferential wall and a terminal edge of the uppermost shell member flange;

the first gasket being positioned between the circumferential wall to the circular array of bolt and washer combinations;

(d) a bottom cover on the entire bottom opening of the vessel and on a lowermost of the shell member flanges, wherein the bottom cover has an inner surface positioned on a second gasket, the second gasket being positioned on the lowermost shell member flange and the second gasket being separated from the lowermost shell member flange by a second end of the liner;

the bottom cover being attached to the lowermost shell member flange by a circular array of bolt and washer combinations extending around and through both the bottom cover and the lowermost shell member flange, the circular array of bolt and washer combinations being positioned between the circumferential wall and a terminal edge of the lowermost shell member flange;

the second gasket being positioned between the circumferential wall to the circular array of bolt and washer combinations;

(e) a first end of the liner being attached to the uppermost shell member flange by a circular array of screw fasteners extending around and through the uppermost shell member flange, wherein the fasteners are positioned between the circular array of bolt and washer combinations and the terminal edge of the uppermost shell member flange; and a second end of the liner being attached to the lowermost shell member flange by a circular array of screw fasteners extending around and through the lowermost shell member flange positioned between the circular array of bolt and washer combinations and a terminal edge of the lowermost shell member flange;

(f) at least one inlet for supplying at least one fluid into the interior cavity;

(g) at least one outlet for discharging at least one fluid from the interior cavity;

(h) wherein the shell further comprises at least one weep hole capable of transmitting gases from between the interior cavity of the vessel and the liner to the outside of the vessel; and (i) wherein the at least one weep hole further comprises at least one fluoropolymer insert which extends through the weep hole and into the vessel.

4. The apparatus of claim 1, 2 or 3, wherein an inner surface of the top cover and an inner surface of the bottom cover comprise a fluoropolymer layer.

5. The apparatus of claim 1, 2 or 3, wherein the vessel contains at least 10 cubic feet of volume.

6. The apparatus of claim 1, 2 or 3, wherein adjacent flanges, or a flange and the top cover, or a flange and the bottom cover are bolted together with spring-loaded washers.

7. The apparatus of claim 1, 2 or 3, wherein the fluoropolymer liner comprises a polymer selected from the group consisting of fluorinated ethylene propylene, poly(vinylidene fluoride), polytetrafluoroethylene, perfluoroalkoxy polymer, ethylene tetrafluoroethylene, ethylene hexafluoropropylene, tetrafluoroethylene-hexafluoropropylene, polychlorotrifluoroethylene, ethylene chlorotrifluoroethylene, polytrifluoroethylene and combinations thereof.

8. The apparatus of claim 1, 2 or 3, further comprising a vacuum device connected to at least one weep hole.

9. The apparatus of claim 1, 2 or 3, further comprising a heater for heating the vessel.

10. The apparatus of claim 9, wherein the heater comprises a steam jacket which surrounds the periphery of the at least one shell member.

11. The apparatus of claim 1, 2 or 3, wherein each shell member, each flange and each cover comprises a material selected from the group consisting of stainless steel, nickel containing alloys, and combinations thereof.

12. The apparatus of claim 1, 2 or 3, wherein at least one shell member is further equipped with an attachment pad having a minimum thickness of about 6.35 mm.

13. The apparatus of claim 1, 2 or 3, wherein each shell member has an internal diameter of about from about 4 feet to about 6 feet.

14. The apparatus of claim 1, 2 or 3, wherein each shell member has a length of from about 7 feet to about 8 feet measured from the outer surface of the first flange to the outer surface of the second flange.

* * * * *